United States Patent
Gindelberger

(10) Patent No.: US 11,242,328 B1
(45) Date of Patent: Feb. 8, 2022

(54) HETEROGENEOUS CATALYST AND METHOD FOR PREPARATION OF AROMATIC TRICYCLIC PYRANS

(71) Applicant: Acid Neutral Alkaline Laboratory, Longview, WA (US)

(72) Inventor: David Gindelberger, Ladue, MO (US)

(73) Assignee: Acid Neutral Alkaline Laboratory, Longview, WA (US)

( * ) Notice: Subject to any disclaimer, the term of this patent is extended or adjusted under 35 U.S.C. 154(b) by 0 days.

(21) Appl. No.: 17/221,556

(22) Filed: Apr. 2, 2021

Related U.S. Application Data

(60) Provisional application No. 63/153,425, filed on Feb. 25, 2021.

(51) Int. Cl.
| | |
|---|---|
| *C07D 311/78* | (2006.01) |
| *B01J 23/745* | (2006.01) |
| *B01J 31/02* | (2006.01) |
| *B01J 31/22* | (2006.01) |
| *B01J 37/00* | (2006.01) |

(52) U.S. Cl.
CPC .......... *C07D 311/78* (2013.01); *B01J 23/745* (2013.01); *B01J 31/0252* (2013.01); *B01J 31/2226* (2013.01); *B01J 31/2239* (2013.01); *B01J 37/0063* (2013.01); *B01J 2531/842* (2013.01)

(58) Field of Classification Search
CPC .. B01J 23/745; B01J 31/0252; B01J 31/2226; B01J 31/2239; B01J 37/0063; B01J 2531/842; B01J 27/053; B01J 27/128; A61K 36/185; C07D 311/78
USPC .................. 549/388; 424/725, 774, 777, 778
See application file for complete search history.

(56) References Cited

U.S. PATENT DOCUMENTS

| | | | | |
|---|---|---|---|---|
| 5,227,537 | A * | 7/1993 | Stoss ...................... | C07C 37/14 568/619 |
| 7,524,881 | B2 * | 4/2009 | Goodwin ................ | A61P 25/22 514/454 |
| 8,222,292 | B2 | 7/2012 | Goskonda et al. | |
| 8,895,078 | B2 * | 11/2014 | Mueller ............... | C07D 311/80 424/725 |
| 9,345,771 | B2 | 5/2016 | Goskonda et al. | |
| 9,630,941 | B2 | 4/2017 | Elsohly et al. | |
| 10,596,124 | B2 | 3/2020 | Kaufman | |
| 2004/0143126 | A1 | 7/2004 | Webster et al. | |
| 2010/0210860 | A1 * | 8/2010 | Erler .................... | C07D 311/80 549/390 |
| 2014/0248379 | A1 * | 9/2014 | Mueller ............... | C07D 311/80 424/725 |
| 2015/0057342 | A1 | 2/2015 | Koren et al. | |
| 2017/0008868 | A1 * | 1/2017 | Dialer ................. | C07D 205/04 |
| 2018/0071210 | A1 | 3/2018 | Wilkhu et al. | |
| 2021/0198224 | A1 * | 7/2021 | Berkowitz ............. | C07C 37/50 |

FOREIGN PATENT DOCUMENTS

| | | |
|---|---|---|
| CA | 2618705 | 5/2007 |
| WO | 2012033478 A1 | 3/2012 |
| WO | 2015184127 A2 | 12/2015 |

* cited by examiner

*Primary Examiner* — Patricia L. Hailey
(74) *Attorney, Agent, or Firm* — Husch Blackwell LLP

(57) ABSTRACT

Provided herein are methods for converting CBD to a product mixture comprising $\Delta^8$-THC, $\Delta^9$-THC, or a combination thereof. The methods provided herein may comprise one or more of (1) a contacting step wherein a starting material comprising CBD, a catalyst comprising an iron (III) salt, and optionally a solvent are added to a reaction vessel, thereby forming a reaction mixture; (2) a conversion step wherein at least a portion of the CBD is converted to THC, thereby forming a product mixture; and (3) optionally, a separation step wherein at least a portion of the catalyst is removed from the product mixture. Advantageously, the methods utilize a catalyst comprising iron (III) sulfate, which is commonly used as a food additive and is generally recognized as safe for human consumption, and do not require the use of catalysts or other reagents that are hazardous to human health.

22 Claims, No Drawings

HETEROGENEOUS CATALYST AND METHOD FOR PREPARATION OF AROMATIC TRICYCLIC PYRANS

BACKGROUND

In recent years, there has been increasing interest in the medicinal properties of cannabinoids, which are a family of chemical compounds derived from the *cannabis* plant. For example, cannabidiol (CBD) has long been used as an antiepileptic medication, and the potential use of CBD to treat other neurological disorders is an area of active research. Likewise, while tetrahydrocannabinol (THC) is known as the principal psychoactive constituent of *cannabis*, recent research has identified potential uses of THC to treat a variety of diseases, including chronic pain, spasticity, and symptoms associated with multiple sclerosis and other neurological disorders.

More recently, research has indicated that different isomers of THC may provide different beneficial effects. For example, $\Delta^8$-THC is a double-bond isomer of $\Delta^9$-THC.

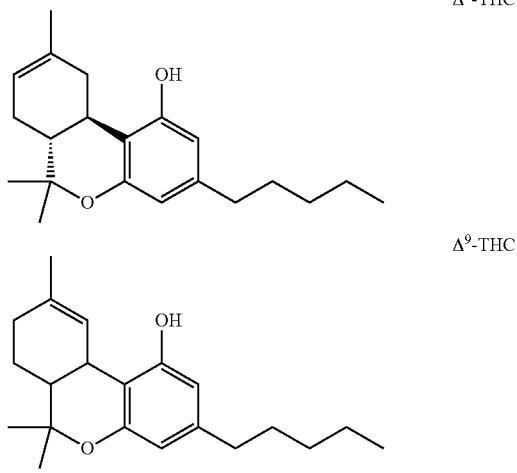

While both isomers are psychoactive, it is currently believed that $\Delta^8$-THC is less potent in this regard than $\Delta^9$-THC. Conversely, $\Delta^8$-THC is believed to be a more potent antiemetic agent than $\Delta^9$-THC.

Industrial hemp comprises CBD in an amount of about 2% by weight, which is significantly greater than either $\Delta^8$-THC (approximately 0.2% by weight) or $\Delta^9$-THC (approximately 0.1% by weight). Methods of converting CBD to $\Delta^8$-THC and $\Delta^9$-THC are therefore desirable. To date, however, a limited amount of research has been performed to identify such methods. For example, U.S. Pat. No. 7,399,872 to Webster et al. utilized a Lewis acid catalyst to promote the conversion of CBD to $\Delta^8$-THC and $\Delta^9$-THC. Unfortunately, the catalysts disclosed by Webster et al. (p-toluenesulfonic acid, boron trifluoride, and $BF_3Et_2O$) are all extremely hazardous to human health. This presents a safety hazard for persons who handle such materials, and also raises concerns about the presence of residual catalyst in the final products, which are intended for human consumption.

It is therefore desirable to develop new methods of efficiently converting CBD to $\Delta^8$-THC and $\Delta^9$-THC. Preferably, such methods would not require the use of catalysts or other reagents that are hazardous to human health. It is further desirable to develop methods that provide an improved degree of control over the relative proportion of $\Delta^8$-THC to $\Delta^9$-THC generated by the reaction.

SUMMARY

Provided herein are methods of converting CBD to THC. The methods provided herein may comprise one or more of (1) a contacting step wherein a starting material comprising CBD, a catalyst comprising an iron (III) salt, and optionally a solvent are added to a reaction vessel, thereby forming a reaction mixture; (2) a conversion step wherein at least a portion of the CBD is converted to THC, thereby forming a product mixture; and (3) optionally, a separation step wherein at least a portion of the catalyst is removed from the product mixture.

For example, provided herein is a method of converting CBD to THC, the method comprising contacting a starting material comprising CBD with a catalyst comprising an iron (III) salt, thereby forming a reaction mixture, and heating the reaction mixture to a temperature of at least about 60° C. for a period of at least about 30 minutes, thereby forming a product mixture comprising THC.

Also provided herein is method of converting CBD to THC, the method comprising (1) a contacting step, wherein a starting material comprising CBD is contacted with a catalyst comprising an iron (III) salt, thereby forming a reaction mixture; and (2) a conversion step, wherein CBD in the reaction mixture is converted to THC, thereby forming a product mixture comprising THC.

Also provided herein is a cannabinoid composition comprising THC, wherein the composition is produced by a method as provided herein.

Other objects and features will be in part apparent and in part pointed out hereinafter.

DETAILED DESCRIPTION

Provided herein are methods for converting CBD to a product mixture comprising THC. Preferably, the product mixture comprises $\Delta^8$-THC, $\Delta^9$-THC, or a combination thereof. The methods utilize a catalyst comprising an iron (III) salt. The iron (III) salt may be, for example, iron (III) sulfate or an iron (III) halide.

For example, in one aspect, the catalyst comprises iron (III) sulfate, which is commonly used as a food additive and is generally recognized as safe for human consumption. Advantageously, the methods described herein do not require the use of catalysts or other reagents that are hazardous to human health.

Definitions

As used herein, CBD refers to cannabidiol.

As used herein, THC refers to tetrahydrocannabinol, and is inclusive of isomers including $\Delta^8$-THC and $\Delta^9$-THC.

As used herein, $\Delta^8$-THC refers to $\Delta^8$-tetrahydrocannabinol.

As used herein, $\Delta^9$-THC refers to $\Delta^9$-tetrahydrocannabinol.

As used herein, iron (III) sulfate (also known as ferric sulfate) refers to the chemical compound having the formula $Fe_2(SO_4)_3$.

As used herein, iron (III) halide refers to a chemical compound having the formula $FeX_3$, where X is a halide anion selected from the group consisting of fluoride, chloride, bromide, or iodide. Specifically, iron (III) fluoride refers to the chemical compound having the formula $FeF_3$, iron (III) chloride refers to the chemical compound having the formula $FeCl_3$, iron (III) bromide refers to the chemical compound having the formula $FeBr_3$, and iron (III) iodide refers to the chemical compound having the formula $FeI_3$.

Components

The methods provided herein may utilize one or more of (1) a starting material comprising CBD; (2) a catalyst comprising an iron (III) salt; and (3) optionally, a solvent. These components are described in further detail below.

Starting Material

The methods provided herein may utilize a starting material comprising CBD. The starting material may comprise, for example, *Cannabis* plant material (e.g., industrial hemp) or an extract thereof.

In preferred embodiments, the starting material comprises substantially pure CBD. For example, the starting material preferably comprises CBD in an amount of at least about 50%, at least about 60%, at least about 70%, at least about 80%, at least about 90%, or at least about 95% by weight.

The starting material may comprise, consist essentially of, or consist of a CBD distillate or CBD isolate. A particularly preferred starting material is CBD isolate.

Iron Catalyst

The methods provided herein may utilize a catalyst comprising an iron (III) salt. The iron (III) salt may be, for example, iron (III) sulfate or an iron (III) halide.

Without being bound to a particular theory, it is currently believed that the iron (III) salts described herein catalyze the conversion of CBD to THC by cationic activation of the exocyclic olefin in CBD. Notably, it has been observed that corresponding iron (II) compounds do not catalyze the conversion of CBD to THC when used in the methods described herein.

In a preferred embodiment, the catalyst comprises iron (III) sulfate.

In some embodiments, the catalyst comprises iron (III) sulfate in the form of a hydrate (i.e., iron (III) sulfate hydrate). For example, the catalyst may comprise a mixture of iron (III) sulfate hydrates and have a total water content of from about 5% to 50% by weight, for example from about 5% to about 40% by weight, from about 10% to about 40% by weight, or from about 10% to about 30% by weight.

Solvent

The methods disclosed herein enable the conversion of CBD to THC without the use of a solvent. In many cases, this represents a significant advantage; if desired, the reaction can be carried out using only two components (e.g., a starting material comprising CBD, and a catalyst comprising iron (III) sulfate).

In some cases, however, the use of a solvent may be desirable. For example, a solvent may improve the ease of processing the product mixture, which can be difficult to work with due to the high viscosity of THC. In some cases, the final product is a dosage form that requires the presence of a solvent, and adding the solvent during the process described herein is therefore convenient. In still further cases, and again without being bound to a particular theory, it is believed that the presence of a solvent may affect the relative amounts of minor cannabinoids (i.e., cannabinoids other than CBD or THC) produced during the conversion step. Non-limiting examples of suitable solvents include alcohols, alkanes, edible oils, and any other emulsifiers or surfactants approved for use in pharmaceutical formulations.

The solvent may comprise an alcohol. The alcohol may be, for example, a $C_1$ to $C_6$ organic alcohol. Non-limiting examples of suitable alcohols include methanol, ethanol, and isopropanol. A preferred solvent is isopropanol.

The solvent may comprise an alkane. The alkane may be, for example, a $C_1$ to $C_{10}$ alkane, more preferably a $C_5$ to $C_8$ alkane. Non-limiting examples of preferred alkanes include hexane and heptane.

The solvent may comprise an edible oil. For example, the solvent may comprise a vegetable oil. A preferred solvent is coconut oil. The use of an edible oil is particularly desirable were the desired final product is an edible formulation. In those cases, an edible oil (e.g., coconut oil) may be used as a solvent and simply carried through into the final, edible formulation.

The solvent may comprise one or more emulsifiers or surfactants approved for use in pharmaceutical formulations. Non-limiting examples of suitable emulsifiers and surfactants include ethoxylated fatty acid derivatives (e.g., polyoxyl stearate) and polysorbate-type nonionic surfactants. For example, the solvent may comprise polyoxyl stearate.

Reaction Procedure

The methods provided herein may comprise one or more of (1) a contacting step wherein a starting material comprising CBD, a catalyst comprising an iron (III) salt, and optionally a solvent are added to a reaction vessel, thereby forming a reaction mixture; (2) a conversion step wherein at least a portion of the CBD is converted to THC, thereby forming a product mixture; and (3) optionally, a separation step wherein at least a portion of the catalyst is removed from the product mixture. These steps are described in further detail below.

Contacting Step

The methods provided herein may comprise a contacting step wherein a starting material comprising CBD, a catalyst comprising an iron (III) salt, and optionally a solvent are added to a reaction vessel, thereby forming a reaction mixture.

The components may be added in any order. Preferably, the starting material is added first, followed by the catalyst, and optionally followed by the solvent.

Optionally the reaction mixture may be stirred (e.g., using a stir bar).

If a solvent is used, the reaction mixture may be heated in order to fully dissolve the CBD in the solvent. The reaction mixture may be heated, for example, to a temperature of at least about 30° C., at least about 40° C., at least about 50° C., or at least about 60° C. in order to dissolve the CBD. Typically, when a solvent is used, the reaction mixture is heated to a temperature of from about 30° C. to about 70° C., from about 40° C. to about 70° C., or from about 45° C. to about 65° C. in order to dissolve the CBD.

Typically, the reaction mixture comprises the starting material in an amount of at least about 50% by weight, for example, at least about 60%, at least about 70%, at least about 80%, at least about 90%, at least about 95%, at least about 96%, at least about 97%, at least about 98%, or even at least about 99% by weight. Correspondingly, the reaction mixture typically comprises CBD in an amount of at least about 80% by weight, for example, at least about 90%, at least about 95%, at least about 96%, at least about 97%, at least about 98%, or even at least about 99% by weight.

The reaction mixture may comprise the catalyst in an amount of from about 0.01% by weight to about 10% by weight, for example, from about 0.1% by weight to about 5% by weight, from about 0.5% by weight to about 5% by weight, or from about 1% by weight to about 5% by weight. Typically, the reaction mixture comprises the catalyst in an amount of less than about 10% by weight, less than about 5% by weight, less than about 4% by weight, less than about 3% by weight, less than about 2% by weight, less than about 1% by weight, less than about 0.5% by weight, or even less than about 0.1% by weight. It has been observed that if the reaction mixture is subjected to mixing, relatively lower amounts of catalyst are preferred, for example from about 0.01% by weight to about 1% by weight, from about 0.01% by weight to about 0.5% by weight, or from about 0.01% by weight to about 1% by weight.

The reactions described herein can be carried out successfully even with very small amounts of catalyst. For example, the reactions have been successfully carried out where the reaction mixture comprises the iron (III) salt in a concentration of less than about 20 parts per million (ppm). For example, the reaction mixture may comprise the iron (III) salt in an amount of less than about 1000 ppm, less than about 500 ppm, less than about 200 ppm, less than about 100 ppm, less than about 75 ppm, less than about 50 ppm, or less than about 25 ppm.

The reaction mixture may comprise CBD and the iron (III) salt in a molar ratio of at least about 20:1, at least about 30:1, at least about 50:1, at least about 100:1, at least about 150:1, at least about 200:1, at least about 300:1, at least about 400:1, at least about 420:1, at least about 440:1, at least about 460:1, at least about 480:1, at least about 500:1, at least about 1000:1, at least about 2000:1, or even at least about 3000:1. For example, the reaction mixture may comprise CBD and the iron (III) salt in a molar ratio of from about 10:1 to about 350:1, such as from about 15:1 to about 100:1, from about 15:1 to about 50:1, or from about 20:1 to about 40:1, or from about 15:1 to about 30:1. In other embodiments, the reaction mixture may comprise CBD and the iron (III) salt in a molar ratio of from about 500:1 to about 5000:1, such as from about 750:1 to about 5000:1, from about 750:1 to about 3500:1, or from about 1000:1 to about 3500:1.

Conversion Step

The methods provided herein may further comprise a conversion step wherein at least a portion the CBD starting material is converted to THC, thereby providing a product mixture comprising $\Delta^8$-THC, $\Delta^9$-THC, or a combination thereof.

The conversion step may comprise heating the reaction mixture. For example, the reaction mixture may be heated to a temperature of at least about 50° C., at least about 60° C., at least about 70° C., at least about 75° C., at least about 80° C., at least about 85° C., or at least about 90° C. Typically, the conversion step is carried out at a temperature of from about 70° C. to about 100° C., for example, from about 75° C. to about 100° C., or from about 75° C. to about 90° C.

The conversion step may comprise heating the reaction mixture for a period of at least about 30 minutes, at least about 1 hour, at least about 1.5 hours, at least about 2 hours, at least about 2.5 hours, at least about 3 hours, at least about 3.5 hours, at least about 4 hours, at least about 4.5 hours, or at least about 5 hours. For example, the conversion step may comprise heating the reaction mixture for a period of from about 30 minutes to about 6 hours, from about 1 hour to about 6 hours, from about 2 hours to about 6 hours, from about 2.5 hours to about 6 hours, or from about 2.5 hours to about 5 hours.

Without being bound to a particular theory, it has been observed that at higher temperatures, the reaction proceeds more rapidly and produces a higher proportion of $\Delta^8$-THC in the product mixture. Higher temperatures may therefore be used to ensure rapid and complete conversion of CBD to $\Delta^8$-THC, if desired.

The conversion step may be carried out under ambient air. Alternatively, the conversion step may be carried out under an atmosphere comprised substantially of nitrogen. As a further alternative, the conversion step may be carried out under vacuum conditions.

Optionally, the progress of the reaction may be monitored by periodically taking samples of the liquid reaction mixture and analyzing them, for example using gas chromatography (GC). For example, the reaction may be monitored by collecting a sample of the reaction mixture every 30 to 60 minutes.

The conversion step may further comprise cooling the reaction mixture to halt the conversion of CBD to THC. The reaction may be stopped by cooling the reaction mixture to a temperature of less than about 65° C., for example, less than about 60° C., less than about 55° C., less than about 50° C., less than about 45° C., or less than about 40° C.

Product Mixture

The conversion step provides a product mixture that comprises $\Delta^8$-THC, $\Delta^9$-THC, or a mixture thereof. The product mixture may further comprise unreacted CBD, and optionally other cannabinoids (which may be referred to herein as minor cannabinoids).

In preferred embodiments of the methods provided herein, at least about 30% by weight of the CBD in the starting material is converted to THC. For example, in preferred embodiments at least about 40% by weight, at least about 50% by weight, at least about 60% by weight, at least about 70% by weight, at least about 80% by weight, or at least about 90% by weight of the CBD in the starting material is converted to THC.

The product mixture may comprise a mixture of $\Delta^8$-THC and $\Delta^9$-THC. In some embodiments, the ratio of $\Delta^8$-THC to $\Delta^9$-THC in the product mixture is approximately 1:1. For example, the ratio of $\Delta^8$-THC to $\Delta^9$-THC in the product mixture may range from about 20:1 to about 0.05:1, from about 10:1 to about 0.1:1, from about 4:1 to about 0.25:1, from about 3:1 to about 0.3:1, from about 2:1 to about 0.5:1, or from about 1.5:1 to about 0.75:1.

In some embodiments, $\Delta^9$-THC comprises a significant percentage of the total amount of THC in the product mixture. For example, $\Delta^9$-THC may comprise at least about 10%, at least about 20%, at least about 30%, at least about 35%, or at least about 40% of the total amount of THC in the product mixture.

In other embodiments, the product mixture may comprise $\Delta^8$-THC in significant excess relative to $\Delta^9$-THC. For example, the product mixture may comprise $\Delta^8$-THC in a ratio, relative to $\Delta^9$-THC, of at least about 2:1, at least about 3:1, at least about 4:1, at least about 5:1, at least about 10:1, at least about 15:1, or even at least about 20:1. In still further embodiment, the product mixture may comprise $\Delta^8$-THC in a ratio, relative to $\Delta^9$-THC, of at least about 50:1, at least about 100:1, at least about 200:1, at least about 300:1, at least about 400:1, or even at least about 500:1.

For example, in some embodiments, $\Delta^8$-THC comprises at least about 70%, at least about 80%, at least about 90%, at least about 95%, at least about 98%, or at least about 99% of the total amount of THC in the product mixture.

Separation Step

The methods provided herein may further comprise a separation step wherein at least a portion of the catalyst is removed from the product mixture.

The separation step is optional. In some embodiments, it may be desirable to retain the iron (III) salt in the product mixture. If the iron (III) salt is not filtered out, it will typically be present in a low concentration (typically less than 100 ppm) in the final, formulated product. This iron content is not harmful, and in some cases may even be desirable for its nutritional value. For example, iron (III) sulfate is often used as a food additive, and is generally regarded as safe for human consumption.

If desired, however, the iron (III) salt may be separated from the reaction product using methods known to those skilled in the art. For example, the iron (III) salt may be removed by filtration.

When a solvent is present, the reaction mixture is preferably cooled prior to filtration. The reaction mixture may be cooled in ambient air, or alternatively by placing a container comprising the reaction mixture into a cool water bath. For example, the reaction mixture may be cooled to a temperature of less than about 70° C., less than about 65° C., or less than about 60° C. prior to filtration. For example, the reaction mixture may be cooled to a temperature of from about 60° C. to about 70° C. prior to filtration.

Alternatively, when no solvents are present, it is preferable to filter the reaction mixture at a relatively warmer temperature. For example, the filtration step may be carried out at a temperature of from about 70° C. to about 80° C.

Cannabinoid Compositions

Also provided herein is a cannabinoid composition comprising THC, wherein the composition is produced by a method as described above.

For example, the cannabinoid composition may comprise a product mixture as described above. The composition may, for example, comprise $\Delta^8$-THC and/or $\Delta^9$-THC in any of the amounts, concentrations, or ratios as described above with respect to the product mixture.

EXAMPLES

The following non-limiting examples are provided to further illustrate the present disclosure.

General Reaction Procedure

The reaction procedure described below was used in each of the following examples, unless otherwise indicated. In general, the reaction converts CBD in the starting material to a mixture of $\Delta^8$-THC and $\Delta^9$-THC.

CBD isolate is placed in a reaction container and a catalyst comprising an iron salt is added. Optionally, a solvent is added and the mixture warmed to above 60° C. The reaction is then run at a temperature between 75° C. and 100° C. The reaction is monitored by gas chromatography (GC), and when the target conversion of CBD to THC is achieved, the reaction is stopped by cooling to a temperature of less than about 60° C. by placing a container comprising the reaction mixture into a cool water bath.

The catalyst is then removed by filtering the reaction mixture with a fritted glass filter or, alternatively with a paper filter in a buchner. When a solvent is present, the reaction mixture is cooled to a temperature of 60° C. prior to filtration. When no solvents are present, the reaction mixture is filtered at a relatively warmer temperature of approximately 80° C., and then cooled further.

Cannabinoids present in the reaction product were identified by gas GC retention time after having established the method with known standards. The ratio of $\Delta^9$-THC to $\Delta^8$-THC in the reaction product was observed to depend on temperature, time and catalyst charge. In some cases, small amounts of other minor cannabinoids were also produced.

In the examples described below, gas chromatography was carried out using a Varian 450-GC equipped with a standard polysiloxane capillary column, a flame ionization detector and a split/splitless injector. Samples were dissolved in a volatile solvent such as ethanol or acetone and injected in 1-2 µl volumes. Varian "Interactive Graphics" 6.9.3 software was used to integrate the FID data.

Example 1

One gram of CBD isolate and 60 mg of Fe(III) sulfate hydrate were charged to a glass vial with a stir bar. Isopropyl alcohol (IPA), 500 was added as a solvent. The mixture was then warmed to 80° C. for 2.5 hours. The cannabinoid content of the product mixture consisted of 51% CBD, 6% $\Delta^8$-THC, and 43% $\Delta^9$-THC.

Example 2

Prior to this reaction, the Fe(III) sulfate hydrate was ground in a mortar and pestle to reduce particle size. One gram of CBD isolate and 50 mg of Fe(III) sulfate hydrate were charged to a glass vial with a stir bar. Hexane, 2 ml, was added as a solvent. The mixture was warmed to 80° C. for 2 hours, and then to 100° C. for 3 hours. The cannabinoid content of the product mixture consisted of 29% CBD, 30% $\Delta^8$-THC, and 40% $\Delta^9$-THC, with the remainder being minor cannabinoids.

Example 3

One gram of CBD isolate and 50 mg of Fe(III) sulfate hydrate were charged to a glass vial with a stir bar. Hexane, 2 ml, was added as a solvent. The mixture was warmed to 80° C. for 2 hours then 100° C. for 3 hours. The cannabinoid content of the product mixture consisted of 29% CBD, 30% $\Delta^8$-THC, and 40% $\Delta^9$-THC, with the remainder being minor cannabinoids.

Example 4

One gram of CBD isolate and 10 mg of Fe(III) sulfate hydrate were charged to a glass vial with a stir bar. No solvent was added. The mixture was warmed to 80° C. for 2 hours. The cannabinoid content of the product mixture consisted of 13% CBD, 65% $\Delta^8$-THC, and 18% $\Delta^9$-THC, with the remainder being minor cannabinoids.

Example 5

One gram of CBD isolate and 5 mg of Fe(III) sulfate hydrate were charged to a glass vial with a stir bar. No solvent was added. The mixture was warmed to 75° C. for 2 hours. The cannabinoid content of the product mixture consisted of 43% CBD, 22% $\Delta^8$-THC, and 34% $\Delta^9$-THC, with the remainder being minor cannabinoids.

Example 6

CBD isolate, 2.5 grams, and 45 mg of Fe(III) sulfate hydrate were charged to a glass vial with a stir bar. Coconut oil, 2.5 grams, was added as a solvent. The mixture was warmed to 80° C. for 4.5 hours. The cannabinoid content of the product mixture consisted of 9% CBD, 80% $\Delta^8$-THC, and 4% $\Delta^9$-THC, with the remainder being minor cannabinoids.

Example 7

CBD isolate, 3 grams, and 45 mg of Fe(III) sulfate hydrate were charged to a glass vial with a stir bar. Polyoxyl stearate, 3 grams, was added as a solvent. The mixture was warmed to 80° C. for 4.5 hours. The cannabinoid content of the product mixture consisted of 39% CBD, 19% $\Delta^8$-THC, and 35% $\Delta^9$-THC, with the remainder being minor cannabinoids.

Example 8

One gram of CBD isolate and 10 mg of Fe(II) sulfate hydrate were charged to a glass vial with a stir bar. No solvent was added. The mixture was warmed to 80° C. for 8 hours. The cannabinoid content of the product mixture consisted entirely of unreacted CBD. This example illustrates that iron (II) sulfate did not work. Several similar attempts, at higher temperatures and in various solvents, also showed no conversion when Fe(II) sulfate hydrate was used as a catalyst.

Example 9

22 grams of CBD isolate and 4 mg of Fe(III) sulfate hydrate were charged to a round-bottomed flask with a stir bar. No solvent was added. The mixture was warmed to 100° C. for 1 hour. The cannabinoid content of the product mixture consisted of 73% CBD, 8% $\Delta^8$-THC, and 15% $\Delta^9$-THC, with the remainder being minor cannabinoids.

Example 10

1.2 grams of CBD isolate and 13 mg of Iron(II,III) hexacyanoferrate(II,III) were charged to a glass vial and capped with a stir bar. No solvent was added. The mixture was warmed to 100° C. for 3 hours. The cannabinoid content of the product mixture consisted of 96% CBD, 2% $\Delta^8$-THC, and 1% $\Delta^9$-THC.

Example 11

1.2 grams of CBD isolate and 18 mg of Iron(III) oxide were charged to a glass vial and capped with a stir bar. No solvent was added. The mixture was warmed to 150° C. for 8 hours. The cannabinoid content of the product mixture consisted of 97% CBD and 3% $\Delta^9$-THC.

Example 12

1.1 grams of CBD isolate and 38 mg of Fe(II) chloride hydrate were charged to a vial with a stir bar. No solvent was added. The vial was capped and the mixture was warmed to 100° C. for 2 hours. The final appearance was a dark yellow oil. The final reaction mixture consisted of 99% CBD, and <1% $\Delta^9$-THC.

Example 13

1.4 grams of CBD isolate and 56 mg of Fe(III) phosphate were charged to a vial with a stir bar. No solvent was added. The vial was capped and the mixture was warmed to 100° C. for 2 hours. The final appearance was a light-yellow oil suspension of the catalyst. The final reaction mixture consisted of 98% CBD, <1% $\Delta^8$-THC and 1% $\Delta^9$-THC.

Example 14

1.4 grams of CBD isolate and 23 mg of Fe(III) chloride were charged to a vial with a stir bar. No solvent was added. The vial was capped and the mixture was warmed to 100° C. for 2 hours. The final appearance was a dark orange oil. The final reaction mixture consisted of 32% CBD, 30% $\Delta^8$-THC and 22% $\Delta^9$-THC, with the remainder being minor cannabinoids.

Example 15

1.1 grams of CBD isolate and 46 mg of Fe(III) stearate were charged to a vial with a stir bar. No solvent was added. The vial was capped and the mixture was warmed to 100° C. for 2 hours. The final appearance was a dark orange oil. The final reaction mixture consisted of 98% CBD, <1% $\Delta^8$-THC and <1% $\Delta^9$-THC.

Example 16

1.2 grams of CBD isolate and 520 mg of Fe(III) ammonium citrate were charged to a vial with a stir bar. No solvent was added. The vial was capped and the mixture was warmed to 90° C. for 1 hour. The final appearance was a dark brown oil. The final reaction mixture consisted of 93% CBD, <1% $\Delta^8$-THC and <2.5% $\Delta^9$-THC, with the remainder being minor cannabinoids.

Example 17

0.9 grams of CBD isolate and 17 mg of Fe(III) oxalate were charged to a vial with a stir bar. No solvent was added. The vial was capped and the mixture was warmed to 90° C. for 4 hours. The final appearance was a light green oil. The final reaction mixture consisted of 98% CBD and <1% $\Delta^8$-THC and 1% $\Delta^9$-THC.

Example 18

0.9 gram of CBD isolate and 16 mg of Fe(III) citrate were charged to a vial with a stir bar. No solvent was added. The vial was capped and the mixture was warmed to 100° C. for 2 hours. The final appearance was a light orange oil. The final reaction mixture consisted of 99% CBD and <1% $\Delta^9$-THC.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. A method of converting CBD to THC, the method comprising:
   (1) a contacting step, wherein a starting material comprising CBD is contacted with a catalyst comprising iron (III) sulfate, thereby forming a reaction mixture; and
   (2) a conversion step wherein at least about 30% by weight of the CBD in the reaction mixture is converted to THC, thereby forming a product mixture comprising THC.

2. The method of claim 1 wherein the catalyst consists essentially of iron (III) sulfate.

3. The method of claim 1 wherein the conversion step comprises stirring the reaction mixture.

4. The method of claim 1 wherein the starting material comprises CBD in an amount of at least about 50% by weight.

5. The method of claim 1 wherein the reaction mixture comprises CBD in an amount of at least about 50% by weight.

6. The method of claim 1 wherein the reaction mixture comprises CBD and the iron (III) salt in a molar ratio of at least about 20:1.

7. The method of claim 1 wherein the reaction mixture comprises CBD and the iron (III) salt in a molar ratio of from about 500:1 to about 5000:1.

8. The method of claim 1 wherein at least about 70% by weight of the CBD in the starting material is converted to THC in the product mixture.

9. The method of claim 1 wherein the product mixture comprises $\Delta^8$-THC and $\Delta^9$-THC.

10. The method of claim 9 wherein the ratio of $\Delta^8$-THC to $\Delta^9$-THC in the product mixture is from about 4:1 to about 0.25:1.

11. The method of claim 9 wherein the ratio of $\Delta^8$-THC to $\Delta^9$-THC in the product mixture is at least about 420:1.

12. The method of claim 1 wherein at least about 10% of the total amount of THC in the product mixture is $\Delta^9$-THC.

13. The method of claim 1 wherein at least about 80% of the total amount of THC in the product mixture is $\Delta^8$-THC.

14. The method of claim 1 wherein the conversion step is conducted under
    (a) a vacuum; or
    (b) an atmosphere consisting essentially of nitrogen.

15. The method of claim 1 wherein the conversion of CBD to THC is monitored by (1) collecting or more samples of the reaction mixture; and (2) analyzing the one or more samples using gas chromatography.

16. The method of claim 1 wherein the reaction mixture further comprises a solvent selected from the group consisting of alcohols, alkanes, edible oils, emulsifiers, and surfactants.

17. The method of claim 1 further comprising a separation step wherein at least a portion of the catalyst is removed from the product mixture.

18. A method of converting CBD to THC, the method comprising:
    (1) a contacting step, wherein a starting material comprising CBD is contacted with a catalyst comprising an iron (III) salt selected from the group consisting of iron (III) sulfate and iron (III) halides, thereby forming a reaction mixture; and
    (2) a conversion step wherein at least about 30% by weight of the CBD in the reaction mixture is converted to THC, thereby forming a product mixture comprising THC,
    wherein the reaction mixture comprises the catalyst in an amount of less than about 10% by weight.

19. The method of claim 18 wherein the reaction mixture comprises the catalyst in an amount of from about 0.01% by weight to about 1% by weight.

20. The method of claim 18 wherein the reaction mixture comprises the catalyst in an amount of less than about 100 ppm.

21. A method of converting CBD to THC, the method comprising:
    contacting a starting material comprising CBD with a catalyst comprising iron (III) sulfate or an iron (III) halide, thereby forming a reaction mixture; and
    heating the reaction mixture to a temperature of at least about 60° C. for a period of at least about 30 minutes; thereby forming a product mixture comprising THC,
    wherein the conversion of CBD to THC is halted by cooling the reaction mixture to a temperature of less than about 50° C.

22. The method of claim 21 wherein the catalyst comprises iron (III) sulfate.

* * * * *